(12) United States Patent
Cree

(10) Patent No.: US 7,695,799 B2
(45) Date of Patent: Apr. 13, 2010

(54) APERTURED LAMINATE AND METHOD OF MAKING

(75) Inventor: James W. Cree, Chesterfield, VA (US)

(73) Assignee: Advantage Creation Enterprise LLC, Chesterfield, VA (US)

( * ) Notice: Subject to any disclaimer, the term of this patent is extended or adjusted under 35 U.S.C. 154(b) by 538 days.

(21) Appl. No.: 11/468,044

(22) Filed: Aug. 29, 2006

(65) Prior Publication Data
US 2007/0048498 A1 Mar. 1, 2007

Related U.S. Application Data

(60) Provisional application No. 60/712,151, filed on Aug. 29, 2005.

(51) Int. Cl.
*B32B 3/24* (2006.01)
*A61F 13/512* (2006.01)

(52) U.S. Cl. ............... 428/137; 428/131; 156/251; 156/252; 604/378; 604/383

(58) Field of Classification Search ........... 428/137, 428/131; 604/378, 383; 156/251, 252
See application file for complete search history.

(56) References Cited

U.S. PATENT DOCUMENTS

| | | | |
|---|---|---|---|
| 3,719,736 A | 3/1973 | Woodruff | |
| 4,223,063 A | 9/1980 | Sabee | |
| 4,629,643 A | 12/1986 | Curro et al. | |
| 4,950,264 A | 8/1990 | Osborn, III | |
| 5,009,653 A | 4/1991 | Osborn, III | |
| 5,336,545 A | 8/1994 | Morman | |
| 5,368,909 A * | 11/1994 | Langdon et al. | 428/137 |
| 5,383,869 A | 1/1995 | Osborn, III | |
| 5,422,172 A | 6/1995 | Wu | |
| 5,494,736 A | 2/1996 | Willey et al. | |
| RE35,206 E | 4/1996 | Hassenboehler, Jr. et al. | |
| 5,575,786 A | 11/1996 | Osborn, III | |
| 5,591,149 A | 1/1997 | Cree et al. | |
| 5,656,119 A | 8/1997 | Srinivasan et al. | |
| 5,674,216 A | 10/1997 | Buell et al. | |
| 5,693,037 A * | 12/1997 | Lee et al. | 604/381 |
| 5,851,935 A | 12/1998 | Srinivasan et al. | |

(Continued)

FOREIGN PATENT DOCUMENTS

EP 0749739 B1 11/2000

(Continued)

OTHER PUBLICATIONS

U.S. Appl. No. 11/739,313, filed Apr. 24, 2007, Piero Angeli et al.

*Primary Examiner*—William P Watkins, III
(74) *Attorney, Agent, or Firm*—Hasse & Nesbitt LLC; Donald E. Hasse

(57) ABSTRACT

A perforated laminate comprising at least first and second layers and apertures extending through at least the first layer. The first layer is a nonwoven or formed film material, and the second layer comprises an absorbent structure. The at least first and second layers are primarily joined at the periphery of the perforated apertures. The laminate is particularly useful as a topsheet for an absorbent article, such as a disposable diaper or sanitary napkin. Also described are various materials and methods used to create such laminates.

22 Claims, 2 Drawing Sheets

U.S. PATENT DOCUMENTS

| | | | |
|---|---|---|---|
| 6,069,097 | A | 5/2000 | Suzuki et al. |
| 6,106,925 | A | 8/2000 | Palumbo |
| 6,190,602 | B1 | 2/2001 | Blaney et al. |
| 6,353,149 | B1 * | 3/2002 | Stone .................. 604/372 |
| 6,395,211 | B1 | 5/2002 | Dettmer et al. |
| 6,537,644 | B1 | 3/2003 | Kauschke et al. |
| 6,610,904 | B1 | 8/2003 | Thomas et al. |
| 6,700,036 | B2 | 3/2004 | Thomas et al. |
| 6,703,115 | B2 | 3/2004 | Hale et al. |
| 6,720,279 | B2 | 4/2004 | Cree et al. |
| 6,752,947 | B1 | 6/2004 | Lanigan et al. |
| 6,849,319 | B2 | 2/2005 | Cree et al. |
| 6,942,748 | B2 | 9/2005 | Cree et al. |
| 2004/0161586 | A1 | 8/2004 | Cree et al. |
| 2007/0029694 | A1 | 2/2007 | Cree et al. |
| 2007/0048498 | A1 | 3/2007 | Cree |
| 2007/0123124 | A1 | 5/2007 | Middlesworth et al. |
| 2007/0237924 | A1 | 10/2007 | Bruce et al. |
| 2007/0249253 | A1 | 10/2007 | Angeli et al. |
| 2007/0259154 | A1 | 11/2007 | Cree |

FOREIGN PATENT DOCUMENTS

| | | |
|---|---|---|
| EP | 1712667 A1 | 10/2006 |
| WO | WO 98/55295 | 12/1998 |

* cited by examiner

US 7,695,799 B2

APERTURED LAMINATE AND METHOD OF MAKING

CROSS-REFERENCE TO RELATED APPLICATIONS

This application claims the benefit of U.S. Provisional Application No. 60/712,151, filed Aug. 29, 2005

TECHNICAL FIELD

The present intention relates to an apertured laminate, more particularly a perforated laminate that comprises at least first and second layers and perforated apertures that extend through at least the first layer. The laminate is particularly useful as a topsheet for absorbent articles, such as disposable diapers or sanitary napkins

BACKGROUND OF THE INVENTION

There has been a need to develop improved topsheets for absorbent articles that are able to recognize the type of fluid discharge and determine whether such fluid should be absorbed entirely by the layer underneath or be redirected along the topsheet surface. This is particularly important for both absorbent sanitary napkins and adult and baby diapers. In the case of sanitary napkins, for example, current products on the market typically only absorb discharged menstrual fluid, and rarely absorb body sweat that remains between the pad and the body. This limitation can create significant discomfort for the wearer. Several patents describe the use of apertures, different material compositions, and laminate structures as a mean to address such issue. However, there is a continuing need for improved perforated laminates for use in absorbent articles.

SUMMARY OF THE INVENTION

The invention relates to a perforated laminate that comprises at least first and second layers and perforated apertures that extend through at least the first layer, said first layer being (1) a nonwoven that has filaments from about 0.2 to about 15 dpf, or (2) a formed film that has a basis weight of from about 15 to about 50 gsm, said second layer comprising an absorbent structure having a median wet pore diameter between about 3 microns and about 50 microns, wherein the at least first and second layers are primarily joined at the periphery of the perforated apertures, and the laminate has a drape test value of from about 30 mm to about 90 mm.

The invention also relates to a method of making the above laminate, and an absorbent article comprising the laminate.

BRIEF DESCRIPTION OF THE INVENTION

DETAILED DESCRIPTION OF THE INVENTION

The present invention relates to a perforated laminate that comprises at least first and second layers and perforated apertures that extend through at least the first layer. The at least first and second layers are primarily joined at the periphery of the perforated apertures, and typically are joined together through entanglement and/or contact bonding.

Figure 1:
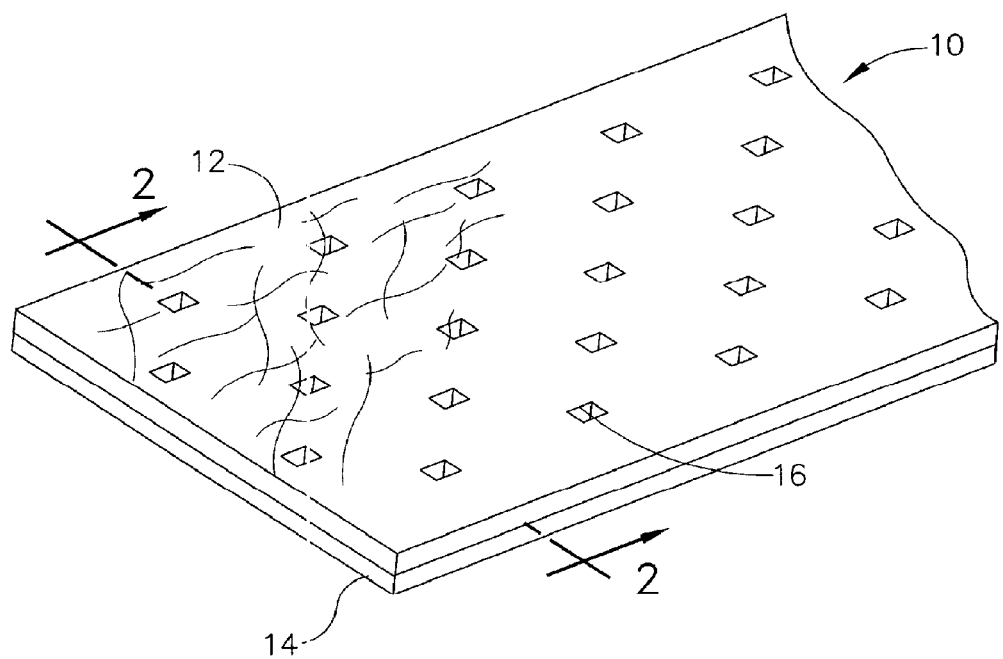
FIG. 1 is a perspective view of a perforated fibrous laminate of the present invention.
Figure 2:
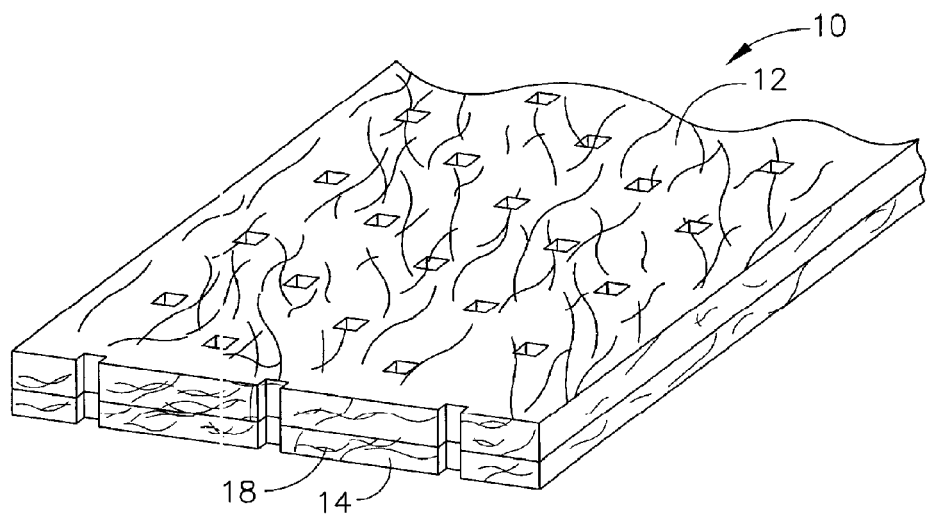
FIG. 2 is an enlarged sectional view of the laminate of FIG. 1.

FIGS. 1 and 2 illustrate such a laminate 10 of the invention comprising a first layer 12, a second layer 14, and apertures 16. The first layer that normally faces the body of the user may be a nonwoven material that typically has a basis weight between about 8 and about 45 grams per square meter (gsm). Alternatively, the first layer may be a formed film material that typically has a basis weight between about 15 and about 50 gsm, more typically between about 18 and about 30 gsm. A nonwoven first layer typically comprises large denier fibers of at least about 0.2 to about 15 denier per filament (dpf), typically in the range of from about 1 to about 10 dpf. The nonwoven layer can comprise any commercially available type of nonwoven such as typically sold as topsheets for absorbent articles (e.g., feminine protection products, baby diapers, etc.), including nonwovens that have a flocked surface. A formed film first layer can be any commercially available type of formed film such as typically sold as topsheets for absorbent articles, including formed films that have a flocked surface.

The second layer comprises any absorbent structure that has a small wet pore diameter, including reticulated foam, wetlaid tissue, airlaid tissue, or nonwoven. These absorbent structures should have a median wet pore diameter between about 3 microns and about 50 microns, typically from about 5 to about 35 microns. The wet pore diameter values are measured according to the method presented in U.S. Pat. No. 5,591,149, Cree et al, incorporated herein by reference. The second layer typically has a basis weight between about 8 and about 70 gsm, are typically from about 10 to about 60 gsm. The perforated laminate of this invention has improved flexibility, and typically has a drape test value of from about 30 mm to about 90 mm, typically from about 40 mm to about 80 mm. The drape test values are measured according to the EDANA 50.6-02 method, incorporated herein by reference.

The perforated laminate may also comprise one or more additional layers. For example, the laminate may comprise a third layer that is below the second layer and has a basis weight between about 5 and about 50 gsm, typically between about 8 and about 45 gsm. The third layer typically comprises large denier fibers of at least about 0.2 to about 15 dpf, more typically from about 1 to about 10 dpf.

Figure 4:
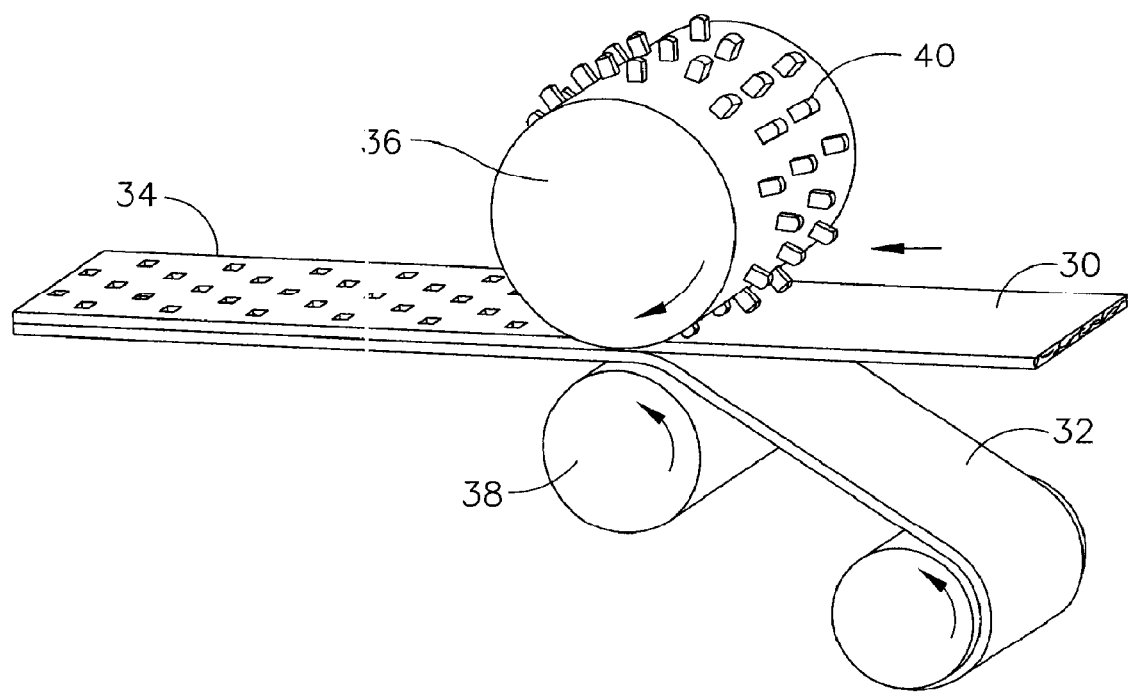
FIG. 4 is a perspective view of the laminate of FIG. 1 being formed by feeding first and second layers of nonwoven materials through calender rolls according to a method of the invention.

As shown in FIG. 4, the laminate can be made by simultaneously feeding the first layer 30 and second layer 32 through perforating calender rolls 36 and 38 under pressure to perforate apertures through at least the first layer. One calender roll, such as roll 36, has protruding perforating surfaces 40 and the other calender roll, such as roll 38, has a surface that is either smooth or has receptacles for the protruding surfaces of roll 36. Roll 38 can be heated, typically to about 300° F. (about 148.9° C.), or cooled and can be either driven by the roll 36 or self-driven in a direction that facilitates the formation of apertures. In another example, the two nonwoven webs are fed through a nip of heated pins and a counter rotating brush roll. In such a case, the pins perforate the two webs and the shear force of the heated pins going through the two materials densifies and bonds the two layers together. The perforated laminate 34 is primarily joined and bonded at the periphery of the perforated apertures. The joining of the two or more layers primarily involves physical entanglement but may also involve partial melting of one or more of the layers. After the bonding is completed, the laminated material, such as laminate 34, can be wound on a roll and shipped to customers for use in the desired product applications.

Figure 3:
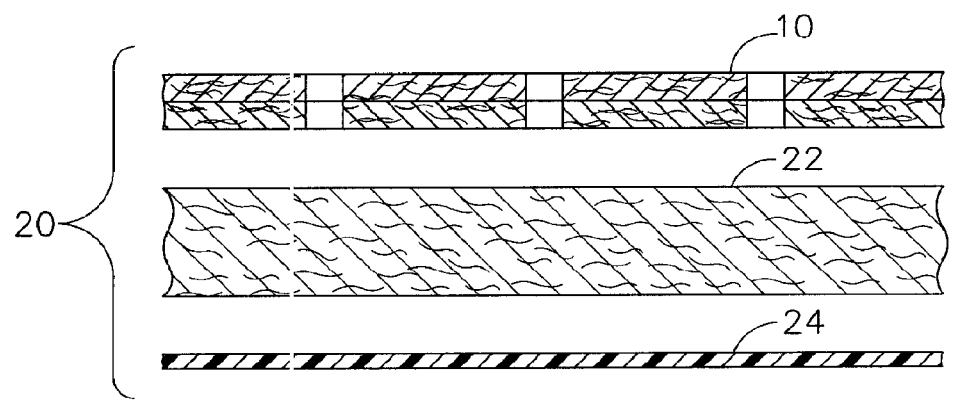
FIG. 3 is an exploded sectional view of an absorbent article comprising the laminate of FIG. 1.

One benefit from the above methods for joining the at least first and second layers is the resultant absorbency of the micropores that form on the walls at the periphery of the perforated apertures. The micropores typically have a median wet pore size of less than about 10 microns, more typically less that about 8 microns. During use of the laminate, these micropores, together with the small pores or capillaries between the filaments of the second layer 14, such as capillaries 18, actively seek to absorb small quantities of fluid and/or fluids with small size particles, such as perspiration on the user's skin or the blood plasma present in menstrual fluid. In such a case, the second layer together with the micropores on the aperture walls act as a filter material absorbing and distributing the small quantities of fluid and/or fluids with small size particles, while the larger apertures of the laminate transfer larger quantities of fluid through the laminate to absorbent layers typically placed under the laminate. The invention thus provides a multifunction laminate that is particularly useful as a topsheet material for absorbent articles. For example, FIG. 3 shows the laminate 10 being used as a topsheet for an absorbent article 20 further comprising an absorbent layer 22 and fluid impermeable backsheet 24. Examples of such absorbent articles are disclosed in U.S. Pat. Nos. 5,383,869, 5,575,786, 4,950,264 and 5,009,653, Osborn III, incorporated herein by reference.

In one embodiment, the first layer is a carded unbonded nonwoven having a basis weight of from about 10 to about 40 gsm, typically about 10 gsm, and comprising about 2.2 dpf polypropylene fibers, such as supplied by Meraklon SRL under the tradename S2000. In another embodiment, the second layer is a pre-bonded, densified, hydrophilic meltblown polypropylene nonwoven, such as available from Atex SRL located in Milano, Italy. The meltblown polypropylene, produced according to methods described in the art, can be formed into two stratum with about equal pore size but different hydrophilicity. In one example, the top stratum of the second layer is hydrophobic and has about 20% of the basis weight of the total meltblown web while the lower stratum of the second layer is rendered hydrophilic through the use of a resin-incorporated surfactant available in the resin package from the 3M Company in St. Paul, Minn. In another embodiment, a first layer is a formed film having a basis weight of between about 18 and about 30 gsm and a mesh of between about 40 and about 120 holes per linear inch (about 15.7 to about 47.2 holes per linear cm), such as KG 001 available from Xiamen Yanjan Industry Co. Ltd. located in Xiamen, China. The second layer in this embodiment is the same meltblown polypropylene nonwoven as described above.

The invention also relates to a method for making a perforated laminate, said method comprising providing a first layer and a second layer as described above, and feeding the first layer and second layer through perforating rolls to perforate apertures through at least the first layer. The at least first and second layers are primarily joined at the periphery of the perforated apertures, and the laminate has a drape test value of from about 30 mm to about 90 mm.

Various embodiments of this invention have been described. However, this disclosure should not be deemed to be a limitation on the scope of the invention. Accordingly, various modifications, adaptations, and alternatives may occur to one skilled in the art without departing from the spirit and scope of the claimed invention.

What is claimed is:

1. A perforated laminate that comprises at least first and second layers and perforated apertures that extend through at least the first layer, said first layer being (1) a nonwoven that has filaments from about 0.2 to about 15 dpf, or (2) a formed film that has a basis weight of from about 15 to about 50 gsm, said second layer comprising a fibrous nonwoven absorbent structure having a median wet pore diameter between about 3 microns and about 50 microns, wherein the at least first and second layers are primarily joined at the periphery of the perforated apertures, the perforated apertures have walls that have micropores having a median wet pore size less than about 10 microns, and the laminate has a drape test value of from about 30 mm to about 90 mm.

2. A perforated laminate according to claim 1 wherein the first layer has a flocked surface.

3. A perforated laminate according to claim 1 wherein the first layer is a nonwoven comprising filaments of from about 1 to about 10 dpf.

4. A perforated laminate according to claim 1 wherein the first layer is a nonwoven that has a basis weight of between about 8 and about 45 gsm.

5. A perforated laminate according to claim 1 wherein the first layer is a formed film that has a basis weight of between about 18 and about 30 gsm.

6. A perforated laminate according to claim 1 wherein the first layer is a formed film that has a mesh of between about 40 and about 120 holes per linear inch.

7. A perforated laminate according to claim 1 wherein the second layer has a basis weight of between about 8 and about 70 gsm.

8. A perforated laminate according to claim 1 wherein the second layer comprises reticulated foam, wetlaid tissue, airlaid tissue, or a nonwoven.

9. A perforated laminate according to claim 1 further comprising a third nonwoven layer below the second layer and having a basis weight between about 8 and about 45 gsm.

10. A perforated laminate according to claim 2 wherein the first layer is a nonwoven that has a basis weight of between about 8 and about 45 gsm, the second layer has a basis weight of between about 8 and about 70 gsm.

11. An absorbent article comprising a perforated laminate that comprises at least first and second layers and perforated apertures that extend through at least the first layer, said first layer being (1) a nonwoven that has filaments from about 0.2 to about 15 dpf, or (2) a formed film that has a basis weight of from about 15 to about 50 gsm, said second layer comprising a fibrous nonwoven absorbent structure having a median wet pore diameter between about 3 microns and about 50 microns, wherein the at least first and second layers are primarily joined at the periphery of the perforated apertures, the perforated apertures have walls that have micropores having a median wet pore size less than about 10 microns, and the laminate has a drape test value of from about 30 mm to about 90 mm.

12. An absorbent article according to claim 11 wherein the first layer is a nonwoven comprising filaments of from about 1 to about 10 dpf.

13. An absorbent article according to claim 11 wherein the first layer is a nonwoven that has a basis weight of between about 8 and about 45 gsm.

14. An absorbent article according to claim 11 wherein the first layer is a formed film that has a basis weight of between about 18 and about 30 gsm.

15. An absorbent article according to claim 11 wherein the first layer is a formed film that has a mesh of between about 40 and about 120 holes per linear inch.

16. An absorbent article according to claim 11 wherein the second layer has a basis weight of between about 8 and about 70 gsm.

17. An absorbent article according to claim 11 wherein the second layer comprises reticulated foam, wetlaid tissue, airlaid tissue, or a nonwoven.

18. An absorbent article according to claim 11 further comprising an absorbent layer and a backsheet.

19. An absorbent article according to claim 18 wherein the first layer is a nonwoven that has a basis weight of between about 8 and about 45 gsm, and the second layer has a basis weight of between about 8 and about 70 gsm.

20. A method for making a perforated laminate, said method comprising providing a first layer being (1) a nonwoven that has filaments of from about 0.2 to about 15 dpf, or (2) a formed film that has a basis weight of at least about 15 to about 50 gsm; providing a second layer comprising a fibrous nonwoven absorbent structure having a median wet pore diameter between about 3 microns and about 50 microns; and feeding said first layer and second layer through perforating rolls to perforate apertures through at least the first layer; wherein the at least first and second layers are primarily joined at the periphery of the perforated apertures, the perforated apertures have walls that have micropores having a median wet pore size less than about 10 microns, and the laminate has a drape test value of from about 30 mm to about 90 mm.

21. A method for making a perforated laminate according to claim 20 wherein the first layer is a nonwoven comprising filaments of from about 1 to about 10 dpf and having a basis weight of between about 8 and about 45 gsm, and the second layer has a basis weight of between about 8 and about 70 gsm.

22. A method for making a perforated laminate according to claim 20 wherein the micropores form on the perforated aperture walls as a result of feeding said first layer and second layer through perforating rolls to perforate apertures through at least the first layer.

* * * * *